US009708570B2

(12) United States Patent
Goeke et al.

(10) Patent No.: US 9,708,570 B2
(45) Date of Patent: Jul. 18, 2017

(54) ORGANIC COMPOUNDS

(71) Applicant: Givaudan, S.A., Vernier (CH)

(72) Inventors: Andreas Goeke, Winterthur (CH);
Philip Kraft, Duebendorf (CH); Yue Zou, Shanghai (CN)

(73) Assignee: Givaudan, S.A., Vernier (CH)

( * ) Notice: Subject to any disclaimer, the term of this patent is extended or adjusted under 35 U.S.C. 154(b) by 0 days.

(21) Appl. No.: 14/900,272

(22) PCT Filed: Jun. 27, 2014

(86) PCT No.: PCT/EP2014/063699
§ 371 (c)(1),
(2) Date: Dec. 21, 2015

(87) PCT Pub. No.: WO2014/207205
PCT Pub. Date: Dec. 31, 2014

(65) Prior Publication Data
US 2016/0369205 A1     Dec. 22, 2016

(30) Foreign Application Priority Data

Jun. 28, 2013 (WO) ................ PCT/CN2013/078376

(51) Int. Cl.
| *A61Q 13/00* | (2006.01) |
| *C07C 47/00* | (2006.01) |
| *C11B 9/00* | (2006.01) |
| *C07C 47/228* | (2006.01) |
| *C07C 47/235* | (2006.01) |
| *A61K 8/33* | (2006.01) |
| *C07C 47/105* | (2006.01) |
| *C07C 47/11* | (2006.01) |
| *C07C 47/232* | (2006.01) |

(52) U.S. Cl.
CPC .............. *C11B 9/0061* (2013.01); *A61K 8/33* (2013.01); *A61Q 13/00* (2013.01); *C07C 47/105* (2013.01); *C07C 47/11* (2013.01); *C07C 47/228* (2013.01); *C07C 47/232* (2013.01); *C07C 47/235* (2013.01); *C07C 2101/02* (2013.01)

(58) Field of Classification Search
CPC ... C07C 47/228; C07C 47/347; C07C 47/453; C11B 9/0061; A61K 8/33; A61Q 13/00
USPC ..................... 568/425, 440; 435/188; 512/21
See application file for complete search history.

(56) References Cited

U.S. PATENT DOCUMENTS

| 3,548,006 A | 12/1970 | Scriabine |
| 5,095,152 A | 3/1992 | Frank |
| 5,527,769 A | 6/1996 | Winter et al. |
| 6,103,688 A | 8/2000 | Winter et al. |
| 6,342,612 B1 | 1/2002 | Sprecker et al. |
| 6,465,410 B1 | 10/2002 | Bettiol et al. |
| 8,754,028 B2 | 6/2014 | Velazquez et al. |
| 2008/0146636 A1 | 6/2008 | Erickson et al. |
| 2009/0099228 A1 | 4/2009 | Aissaoui et al. |
| 2010/0152083 A1 | 6/2010 | Velazquez et al. |
| 2011/0021589 A1 | 1/2011 | Vacher et al. |
| 2012/0209031 A1 | 8/2012 | Lanver et al. |
| 2014/0234244 A1 | 8/2014 | Zenhausern |
| 2014/0296225 A1 | 10/2014 | Tang et al. |
| 2016/0075627 A1 | 3/2016 | Goeke et al. |
| 2016/0108342 A1 | 4/2016 | Goeke et al. |

FOREIGN PATENT DOCUMENTS

| FR | 1.460.826 A | | 1/1966 |
| FR | 1.430.164 A | | 3/1966 |
| GB | 988502 | | 4/1965 |
| GB | 1057360 | * | 2/1967 |
| GB | 2 079 751 A | | 1/1982 |
| JP | 3-221599 | | 9/1991 |
| WO | WO 94/27946 A1 | | 12/1994 |
| WO | WO 2008/065021 A1 | | 6/2008 |
| WO | WO 2009/027957 A2 | | 3/2009 |
| WO | WO 2010/091969 A1 | | 8/2010 |
| WO | WO 2010/105873 A2 | | 9/2010 |
| WO | WO 2011/048068 A2 | | 4/2011 |
| WO | WO 2012/120070 A1 | | 9/2012 |
| WO | WO 2012/172122 A2 | | 12/2012 |
| WO | WO 2013/045301 A1 | | 4/2013 |
| WO | WO 2013/062892 A1 | | 5/2013 |

OTHER PUBLICATIONS

PCT/CN2013/078376—International Search Report, mailed Mar. 27, 2014.
PCT/CN2013/078376—International Written Opinion, mailed Mar. 27, 2014.
PCT/CN2013/078376—International Preliminary Report on Patentability, issued Dec. 29, 2015.
PCT/EP2014/063699—International Search Report, mailed Dec. 9, 2014.
PCT/EP2014/063699—International Written Opinion, mailed Dec. 9, 2014.
PCT/EP2014/063699—International Preliminary Report on Patentability, issued Dec. 29, 2015.
Itooka, et al., "Rhodium-Catalyzed 1,4-Addition Of Arylboronic Acids To α, β-Unsaturated Carbonyl Compounds: Large Accelerating Effects Of Bases And Ligands", The Journal of Organic Chemistry, Jul. 2, 2003, pp. 6000-6004, vol. 68, Issue 15. (Abstract only).
Lamboley, et al., "Synthesis And Properties Of Conformationally Constrained Analogues Of Floral-Type Oderants", Helvetica Chimica ACTA, Jul. 1, 2004, pp. 1767-1793, vol. 87, No. 7.
McCune, et al., "Inhibition Of Hepatic Gluconeogenesis And Lipogenesis By Benzoic Acid, p-tert.-Butylbenzoic Acid, And A Structurally Related Hypolipidemic Agent Sc-33459", Archives of Biochemistry and Biophysics, pp. 124-133, Mar. 1982, vol. 214, Issue 1. (Abstract only).

(Continued)

*Primary Examiner* — T. Victor Oh
(74) *Attorney, Agent, or Firm* — Curatolo Sidoti Co., LPA; Joseph G. Curatolo; Salvatore A. Sidoti

(57) ABSTRACT meta-Substituted 3-phenylpropanal derivatives useful in providing watery-marine, floral-aldehydic notes.

12 Claims, No Drawings

(56) References Cited

OTHER PUBLICATIONS

Skouroumounis, et al., "Synthesis of 1,3,4,5-Tetrahydro-2-Benzoxepin Derivatives As Conformationally Restricted Analogues Of Cyclamenaldehyde-Type Compounds And As Intermediates For Highly Odour-Active Homologues", Helvetica Chimica ACTA, Jan. 1, 1996, pp. 1095-1109, vol. 79, No. 4.

Aronica, et al., "Silylation-Desilylation Of Propargyl Amides: Rapid Synthesis Of Functionalised Aldehydes And β-Lactams", Tetrahedron, Apr. 25, 2007, pp. 6843-6854. vol. 63, No. 29, Elsevier Science Publishers, Amsterdam, NL.

Cagen, et al. "Toxicity Induced By Subchronic Dermal Exposure To Paratertiary Butyl Benzoic Acid (pt BBA) In Fischer 344 Rats", International Journal of Toxicology, Sep./Oct. 1989, pp. 1027-1038, vol. 8, No. 5.

Cheng, et al., "Arylation Of Aldehyde Homoenolates With Aryl Bromides", Organic Letters, Apr. 24, 2013, pp. 2298-2301, vol. 15, No. 9.

Hunter, et al., "Studies On The Oral Toxicity Of p-tert-Butyl Benzoic Acid In Rats", Food and Cosmetics Toxicology, 1965, pp. 289-298, vol. 3. (Abstract only).

Kologrivova, et al., "Isomeric Composition of Aliphatic-Aromatic Aldehydes Obtained From Unsaturated Aldehydes and Aromatic Hydrocarbons", TRUDY/VSESOJUZNYJ NAUCNO-ISSLEDOVATEL'SKIJ INSTITUT SINTETICESKICH I NATURAL'NYCH DUSISTYCH VESCESTV, MINISTERSTVO PROMYSLENNOSTI PRODOVOL'STVENNYCH TOVAROV, MPPT, SSSR, PISCEPROMOIZDAT, USSR, Jan. 1, 1971, pp. 96-101, vol. 9.

Winter, et al., "Synthesis And Odor Properties Of Substituted Indane-2-Carboxaldehydes, Discovery Of A New Floral (Muguet) Fragrance Alcohol", Helvetica Chimica ACTA, Dec. 1 2005, pp. 3118-3127, vol. 88. No. 12.

\* cited by examiner

ORGANIC COMPOUNDS

CROSS REFERENCE TO RELATED APPLICATIONS

This application is a national stage application of International Application No. PCT/EP2014/063699, filed 27 Jun. 2014, which claims priority from International Patent Application No. PCT/CN2013/078376, filed 28 Jun. 2013, which applications are incorporated herein by reference.

The present invention relates to novel compounds possessing watery-marine, floral-aldehydic olfactory properties of high substantivity and residuality. The invention furthermore refers to methods for their production, and to flavour and fragrance compositions and perfumed articles containing these.

In addition to established older perfumery materials such as Calone 1951 and Conoline, many novel marine odorants such as Aldolone, Cascalone, Transluzone and Azurone have been introduced recently. These new odorants, and especially Cascalone and Azurone, led to a renewal of the marine trend that originated in the early 1990s with such launches as 'New West for Her' (Aramis, 1990) and 'Escape' (Calvin Klein, 1991). In addition, the marine, aquatic notes of these odorants became more frequently used to replace the freshness and the aquatic effect of substantive lily-of-the-valley aldehydes, which face certain use restrictions, such as Cyclohexal (4-(4-hydroxy-4-methylpentyl) cyclohex-3-enecarbaldehyde, Lyral). Yet, lacking the floralcy of the respective lily-of-the-valley odorants and some of their freshness, this substitution scheme is somewhat limited. Besides, some algae-like connotations in the odour profile of these 2H-benzo[b][1,4]dioxepin-3(4H)-one derivatives, limit their use in higher concentrations for more pronounced marine effects.

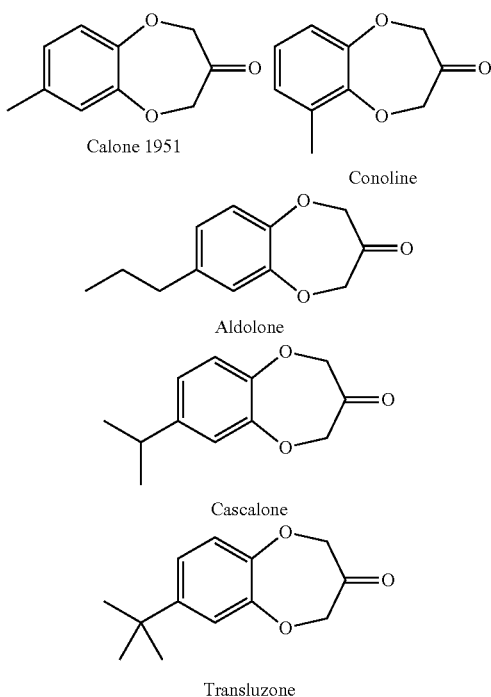

Calone 1951

Conoline

Aldolone

Cascalone

Transluzone

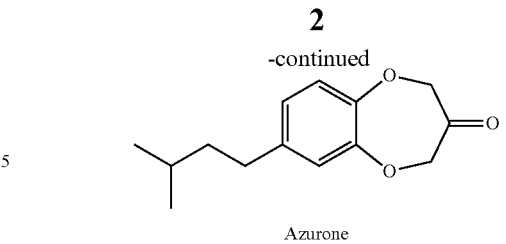

Azurone

Thus, to allow a broader application in perfumery, there is a high demand for new watery-marine odorants with a prominent floral-aldehydic character. Surprisingly, we have now found a small class of novel, meta-substituted 3-phenylpropanal derivatives that posses very typical and characteristic watery-marine notes with fresh floral-aldehydic characters. The watery-marine olfactory properties of these meta-substituted 3-phenylpropanal derivatives were completely unexpected as they bear no structural relationship to the established marine compounds which all possess a 2H-benzo[b][1,4]dioxepin-3(4H)-one skeleton.

Accordingly, in a first embodiment, there is provided the use as fragrance of flavour of a compound of formula (I)

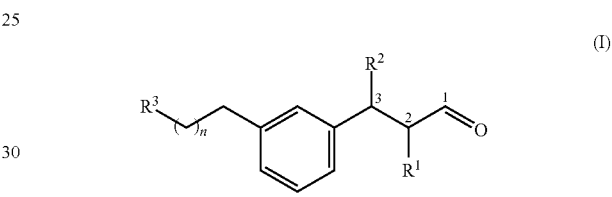

wherein
$R^1$ and $R^2$ are independently selected from hydrogen and methyl with the proviso that at least either $R^1$ or $R^2$ is methyl;
$R^3$ is selected from prop-2-yl, propen-2-yl and cyclopropyl; and
n is 1 or 2.

The compounds of the present invention possess stereocenters at the respectively substituted carbon atom C-2 or C-3, and without asymmetric synthesis, stereoisometric mixtures are obtained, which may be resolved into enantiomerically pure isomers. Resolving stereoisomers adds to the complexity of production of these compounds, and so it is preferred to use the compounds as mixtures of their stereoisomers. There is, however, also the more economical method of employing asymmetric synthesis by asymmetric Hayashi-Miyaura addition of the respective arylboronic acid to the α, β-unsaturated aldehyde, as described for example by R. Itooka et al. [R. Iguchi, N. Miyaura, *J. Org. Chem.* 2003, 68, 6000-6004].

Non-limiting examples are compounds of formula (I) wherein $R^2$ is methyl and $R^3$ is prop-2-yl or cyclopropyl.

Inventors found that, beside the remarkable odor characteristics, the compounds of formula (I) wherein $R^2$ is methyl do not undergo an enzyme-mediated degradation to the corresponding benzoic acid derivative, and thus particular preferred.

Further non-limiting examples are compounds of formula (I) wherein $R^1$ is a methyl and $R^3$ is prop-2-yl or cyclopropyl.

One may cite 3-(3-(2-cyclopropylethyl)phenyl)-2-methylpropanal, not only possessing a remarkable odor characteristic but also possesses a very low odor threshold, which allows its use in very small amounts to achieve an effect.

Further, non-limiting examples are compounds of formula (I) enriched in the (S) enantiomer, preferably by at least 50% ee or higher (for example, at least 70, 80, 90 or 95% ee), and the pure (S) enantiomer of compounds of formula (I).

As a typical example one may cite (S)-3-(3-(4-methylpentyl)phenyl)butanal, possessing a watery-marine, floral-aldehydic, fatty-buttery, slightly metallic, green citrus note. The (S) enantiomer is more powerful (having an about 5-times lower odor threshold) and more marine smelling enantiomer compared to its (R) enantiomer. The lower odor threshold enables perfumers to create desirable fragrances accords with lower concentrations of materials, and is thus preferred.

Further, non-limiting examples are compounds of formula (I) selected from 3-(3-(4-methyl-pentyl)phenyl)butanal, 3-(3-isopentylphenyl)-butanal, 3-(3-(2-cyclopropylethyl)phenyl)butanal, 3-(3-isopentylphenyl)butanal, 3-(3-isopentylphenyl)-2-methylpropanal, 3-(3-(2-cyclopropylethyl)phenyl-2-methylpropanal, 3-(3-(2-cyclopropylethyl)phenyl)butanal, and 2-methyl-3-(3-(3-methylbut-3-en-1-yl)phenyl)butnanal.

The compounds of formula (I) may be used alone, as mixtures thereof, or in combination with a base material. As used herein, the 'base material' includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, 'fragrance composition' means any composition comprising at least one compound of formula (I) and a base material, e.g. a diluent conventionally used in conjunction with odorants, such as dipropylene glycol (DPG), isopropyl myristate (IPM), triethyl citrate (TEC) and alcohol (e.g. ethanol).

The following list comprises examples of known odorant molecules, which may be combined with the compounds of the present invention:
  essential oils and extracts, e.g. castoreum, costus root oil, oak moss absolute, geranium oil, free moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil or ylang-ylang oil;
  alcohols e.g. cinnamic, alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;
  aldehydes and ketones, e.g. Azurone® (7-(3-methylbutyl)-1,5-benzodioxepin-3-one), anisaldehyde, α-amyl-cinnamaldehyde, Georgywood™, hydroxycitronellal, Iso E® Super, Isoraldeine®, Hedione®, Lilial®, maltol, methyl cedryl ketone, methylionone, verbenone, or vanillin;
  ether and acetals, e.g. Ambrox®, geranyl methyl ether, rose oxide, or Spirambrene®;
  esters and lactones, e.g. benzyl acetate, cedryl acetate, γ-decalactone, Helvetolide®, γ-undercalactone or vetivenyl acetate;
  macrocycles, e.g. Ambrettolide, ethylene brassylate or Exaltolide®; and
  heterocycles, e.g. isobutylchinoline.

The compounds according to formula (I) may be used in a broad range of fragranced articles, e.g. in any field of fine and functional perfumery, such as perfumes, air care products, household products, laundry products, body care products and cosmetics specific article and on the nature and quantity of other odorant ingredients. The proportion is typically from 0.0001 to 30 weight percent of the article. In one embodiment, compounds of the present invention may be employed in a fabric softener in an amount of from 0.001 to 3 weight percent. In another embodiment, compounds of the present invention may be used in fine perfumery in amounts from 0.01 to 20 weight percent (e.g. up to about 10 weight percent), more preferably between 0.01 and 5 weight percent. However, these values are given only by way of example, since the experienced perfumer may also achieve effects or may create novel accords with lower or higher concentrations.

The compounds as described hereinabove may be employed in a consumer product base simply by directly mining at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application or an external stimulus such as light, enzyme, or the like, and then mixed with the consumer product case.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odour notes of a consumer product base will be improved, enhanced, or modified.

Thus, the invention furthermore provides a method for improving, enhancing or modifying a consumer product base by means of the addition thereto of an olfactorily acceptable amount of at least one compound of formula (I).

The invention also provides a fragranced article comprising:
  a) as odorant at least one compound of formula (I); and
  b) a consumer product base.

As used herein, 'consumer product base' means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwater, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by of example less than 5% of less than 2% by weight, but additionally include compounds such as acetaldehyde (in particular, for <0.5% by weight), isopropyl alcohol (in particular, <5% by weight), mineral oil (in particular, <5% by weight), and propellants) and cosmetics.

Cosmetic products include:—
(a) cosmetic skincare products, especially bath products, skin washing and cleansing products, skincare products, eye makeup, lip care products, mail care products, intimate care products, foot care products:
(b) cosmetic products with specific effects, especially sunscreens, tanning products, de-pigmenting products, deodorants, antiperspirants, hair removers, and shaving products;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

This list of products is given by way of illustration, and is not to be regarded as being in any way limiting.

To the best of our knowledge none of the compounds of formula (I) as defined herein above has been described in literature before. Thus there is provided in a further aspect of the invention of compound of formula (I)

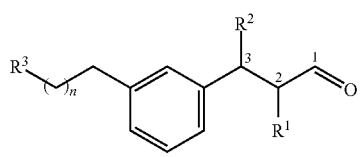

(I)

wherein
$R^1$ and $R^2$ are independently selected from hydrogen and methyl with the proviso that at least either $R^1$ or $R^2$ is methyl;
$R^3$ is selected from prop-2-yl, propen-2-yl and cyclopropyl; and
n is 1 or 2.

The compounds of formula (I) of the invention may be prepared by Hayashi-Miyaura coupling of a suitable arylboronic acid to the respective α,β-unsaturated aldehydes such as crotonaldehyde. This can be carried out in a racemic or enantioselective fashion. Alternatively, the alk(en)yl side chain can also be constructed by Sonogashira coupling, and the optionally methyl substituted propanal moiety by aldol chemistry with elimination and hydrogenation of the conjugate double-bond. Yet another option is the palladium-catalyzed Heck coupling of the respective haloarences with allylic alcohols such as for instance but-2-en-1-ol and 2-methylprop-2-en-1-ol.

The invention is now further described with reference to the following non-limiting examples. These examples are for the purpose of illustration only, and it is understood that variations and modifications can be made by one skilled in the art.

EXAMPLE 1

3-(3-(4-Methylpentyl)pheyl)butanal

Magnesium turnings (5.91, 243 mmol) was added to 20 mL of anhydrous ether in a 250 mL three-necked flask. Under argon atmosphere, initially 5 mL of a solution of 1-bromo-3-methylbutane (36.7 g, 243 mmol) in either (100 mL) was added with occasional heating to 40° C. to initiate the reaction. After the reaction had started, the mixture was allowed to cool to 5° C. in an ice-water bath, and the rest was added dropwise with vigorous stirring within 30 min. After complete addition, the reaction was refluxed for 30 min.

Under argon atmosphere, the prepared Grignard reagent was transferred into a 500 mL-dropping funnel, and, at 5° C. in an ice-water bath added with vigorously stirring within 60 min to a solution of 3-bromobenzaldehyde (30 g, 162 mmol) in ether (50 mL) in a 500 mL three-necked flask, keeping the temperature below 15° C. After completion of the addition, the reaction was reflux for 10 min, and the allowed to cool to 5° C., prior to quenching by dropwise addition of sat. aq. $NH_4Cl$ (150 mL). The organic layer was separated, and the aqueous one extracted with ether (50 mL). The combined organic layers were washed with brine (50 mL) once, and then dried with $MgSO_4$. The solvent was removed on a rotatory evaporator to afford 43.0 g (91%) of 1-(3-bromophenyl)-4-methylpentan-1-ol as a slightly yellowish liquid.

The prepared 1-(3-bromophenyl)-4-methylpentan-1-ol (43 g, 88% purity, 147 mmol) was taken up in toluene (150 mL) in a 250 mL round-bottomed flask, and toluene sulfonic acid hydrate (2.80 g, 14.71 mmol) was mmol) was added. Under argon atmosphere, the resulting colorless solution was refluxed via a Dean-Stark water separator (oil bath: 135° C.). After 2 h of refluxing, no further water was separated, and GC analysis indicated the completion of the conversion. The heating was this removed, and the reaction mixture allowed to coold down to room temperature. A slurry of $NaHCO_3$ (10.0 g) in a little amount of water was then added with vigorously stirring. After 10 min, of stirring, the insoluble mater was filtered off, and rinsed twice with toluene. The filtrate was collected and concentrated to afford 39.8 g of a yellowish liquid, which was further purified by Kugelrohr distillation to provide 34.7 g (99%) of (E)-1-bromo-3-(4-methylpent-1-en-1-yl)benzene as a colorless liquid.

$^1$H NMR (CDCl$_3$): δ=0.95 (d, J=6.6 Hz, 6H, 2 CH$_3$), 1.63-1.80 (m, 1H, (CH$_3$)$_2$CH—), 2.08 (dd, J=6.4 Hz, 6.4 Hz, 2H, —CH$_2$—), 6.14-6.35 (m, 2H, Ar—CH═CH—), 7.08-7.33 (m, 3H, 3 Ar—H), 7.48 (s, 1H, Ar—H). $^{13}$C NMR (CDCl$_3$): δ=22.4 (q), 28.5 (d), 42.4 (t), 122.7 (s), 124.7 (d), 128.8 (d), 129.5 (d), 129.6 (d), 129.9 (d), 131.6 (d), 140.1 (s), MS: m/z (%)=43 (5), 69 (5), 89 (4), 116 (100), 182 (31), 184 (31), 195 (14), 197 (14), 238 (17), 240 (17) [M$^+$].

A 1.6 M solution of butyl lithium in hexane (52 mL, 83 mmol) was added at −78° C. in an acetone-dry ice bath dropwise to a solution of (E)-1-bromo-3-(4-methylpent-1-en-1-yl)benzene (18.0 g, 75.3 mmol in THF (80 mL) in such a way as to keep the reaction temperature below −60° C. After the addition was complete, the reaction mixture was stirred at −78° C. for 30 min, before a solution trimethyl borate (8.6 g, 83 mmol) in THF (20 mL) was added dropwise with stirring at the same temperature. After the addition was complete, the temperature was allowed to raise to 0° C. in the period of 1 h. The reaction was then quenched by addition of 2 N aq hydrogen chloride (75 mL, 150 mmol). The organic layer was separated, and the aqueous one was extracted with tert-butyl methyl ether (2×50 mL). The combined organic layers were washed with brine, and then dried with MgSO$_4$, the solvent was removed in a rotatory evaporator, and the resulting residue was dried under vacuum to give 15.0 g of a yellow solid. This was re-crystalized from isohexane and tert-butyl methyl ether (MTBE) to afford 10.5 g (68% of (E)-(3-(4-methylpent-1-en-1-yl)phenyl)boronic acid as a white solid (Melting point: 113.4-116.7° C.

$^1$H NMR (CDCl$_3$): δ=0.99 (d, J=6.6 Hz, 6H, 2 CH$_3$), 1.72-1.87 (m, 1H, (CH$_3$)$_2$CH—), 2.16 (dd, J=6.8 Hz, 6.8 Hz, 2H, —CH$_2$—), 6.26-6.39 (m, 1H, ArCH=CH—), 6.50 (d, J=15.8 Hz, 1H, Ar—CH=CH—), 7.44 (dd, J=7.6 Hz, 7.2 Hz, 1H, Ar—H); 7.59 (d, J=7.6 Hz, 1H, Ar—H), 8.06 (d, J=7.2 Hz, 1H, Ar—H), 8.16 (s, 1H, Ar—H). $^{13}$C NMR (CDCl$_3$): δ=22.5 (q), 28.7 (d), 42.5 (t), 128.2 (d), 129.9 (d), 130.2 (d), 130.7 (d), 133.4 (d), 134.1 (d), 137.5 (s).

To a solution of potassium phosphate (8.32 g, 39.2 mmol) in dioxane (60 mL) and water (10 mL) in a 250 mL round-bottomed flask was added with stirring [RhCl(cod)]$_2$ (0.0097 g, 0.020 mmol) and cycloocta-1,5-diene (0.328 g, 3.53 mmol), followed by (E)-(3-(4-methylpent-1-en-1-yl)phenyl)boronic acid (8.00 g, 39.2 mmol) and crotonaldehyde (3.30 g, 47.0 mmol). Under an atmosphere of argon, the resulting reaction mixture was then heated to 55° C. for 12 h, and allowed to cool to room temperature. After dilution with water (50 mL), the product was extracted with MTBE (2×50 mL). The combined organic layers were washed with brine, and then dried with MgSO$_4$. The solvent was removed on the rotatory evaporator, and the crude product was purified by column chromatography (isohexane:MTBE, 20:1) and Kugelrohr distillation to provide 7.30 g (81%) of (E)-3-(3-(4-methylpent-1-en-1-yl)phenyl)butanal as a colorless odoriferous liquid.

Odor description; aldehydic, watery-marine, metallic facets:

$^1$H NMR (CDCl$_3$): δ=0.94 (d, J=6.4 Hz, 6H, 2 CH$_3$), 1.31 (d, J=6.9 Hz, 3H, CH$_3$), 167-1.81 (m, 1H, (CH$_3$)$_2$CH—), 2.09 (dd, J=6.8 Hz, 6.8 Hz, 2H, (CH$_3$)$_2$CH—CH$_2$—CH=CH—Ar), 2.60-2.81 (m, 2H, —CH$_2$—CHO), 3.27-3.41 (m, 1H, Ar—CH(CH$_3$)—CH$_2$—), 6.15-6.27 (m, 1H, Ar—CH=CH—), 6.35 (d, J=15.9 Hz, 1H, Ar—CH=CH—), 7.03-7.08 (m, 1H, Ar—H), 7.17-7.27 (m, 3H, Ar—H), 9.69-9.73 (m, 1H, CHO). $^{13}$C NMR (CDCl$_3$): δ=22.1 (q), 22.4 (q), 28.6 (d), 34.3 (d), 42.4 (t), 551.7 (t), 124.1 (d), 124.5 (d), 125.2 (d), 128.8 (d), 130.1 (d), 130.7 (d), 138.3 (s), 145.6 (s), 201.9 (d), MS: m/z (%)=91 (7), 115 (16), 128 (24), 143 (100), 159 (5), 174 (8), 188 (5), 230 (27) [M$^+$].

In a 250 mL round-bottomed flask, (E)-3-(3-(4-methyl-pent-1-en-1-yl)phenyl)butanal (6.00 g, 26 mmol) was dissolved in ethyl acetate (50 mL). The resulting colorless solution was degased, and purged with argon. 10%-Palladium on charcoal (500 mg, 0.470 mmol) was added, and the resulting reaction mixture was stirred under hydrogen atmosphere for 2 h until GC control indicated completion of the conversion. The insoluble material was removed by filtration through a small pad of silica gel, and rinsed with ethyl acetate. The filtrate was collected and concentrated under reduced pressure on a rotatory evaporator. The resulting residue was purified by Kugelrohr distillation to provide 5.40 g (89%) of 3-(3-(4-methylpentyl)phenyl)butanal as a colorless odoriferous liquid.

Odor description: watery-marine, floral-aldehydic, slightly metallic and reminiscent of green lemon.

IR (neat): 2954, 2929, 1725, 1606, 1488, 1459, 792, 705 cm$^{-1}$, $^1$H NMR (CDCl$_3$): δ=0.80 (d, J=6.6 Hz, 6H, 2 CH$_3$), 1.10-1.19 (m, 2H, Ar—CH$_2$—CH$_2$—CH$_2$—), 1.23 (d, J=6.9 Hz, 3H, CH$_3$), 1.44-1.58 (m, 3H, (CH$_3$)$_2$CH—CH$_2$—CH$_3$—). 2.49 (dd, J=7.9 Hz, 7.9 Hz, 2H, —CH$_2$—CH$_2$—Ar), 2.51-2.71 (m, 2H, —CH$_2$—CHO), 3.18-3.28 (m, 1H, Ar—CH(CH$_3$)—CH$_2$—), 6.92-6.98 (m, 3H, Ar—H), 7.10-7.17 (m, 1H, Ar—H), 9.60-9.65 (m, 1H, CHO). $^{13}$C NMR (CDCl$_3$): δ=22.2 (q), 22.6 (q), 27.9 (d), 29.4 (t), 34.3 (d), 36.3 (t), 38.7 (t), 51.8 (t), 123.9 (d), 126.6 (d), 126.9 (d), 128.6 (d), 143.4 (s), 145.4 (s), 202.0 (d). MS: m/z (%)=43 (37), 77 (9), 91 (63), 105 (60), 119 (68), 129 (14), 147 (100), 161 (6), 173 (8), 190 (33), 217 (16), 232 (73) [M$^+$].

The (R)- and (S)-enantiomer of 3-(3-(4-methylpentyl)phenyl)butanal were synthesized by Hayashi-Miyaura reaction according to [R. Itooka, Y. Iguchi, N. Miyaura, J. Org. Chem. 2003, 68, 6000-6004] from (E)-3-(4-methylpent-1-en-1-yl)phenyl)boronic acid (2.0 g, 9.80 mmol) and (E)-but-2-enal (0.69 g, 9.80 mmol) employing [Rh(S-BINAP)(nbd)]BF$_4$ (0.132 g, 0.147 mmol) or [Rh(R-BINAP)(nbd)]BF$_4$ (0.132 g, 0.147 mmol) as catalyst, respectively, followed by a hydrogenation procedure analogous to that described above. The following data were obtained:

(R)-3(3-(4-Methylpentyl)phenyl)butanal (1.0 g, 44% yield, 84% ee). [α]$_D^{22}$=−21.1 (c=1.062 in EtOH).

Odor description: floral-aldehydic, fatty-buttery, sweet-fruity in melon direction, less marine and less powerful than the (S)-isomer.

(S)-3-(3-(4-Methylpentyl)phenyl)butanal (0.70 g, 31% yield, 87% ee). [α]$_D^{22}$=+21.6 (c=1.065 in EtOH).

Odor description: watery-marine, floral-aldehydic, fatty-buttery, slightly metallic, green citrus.

EXAMPLE 2

3-(3-Isopentylphenyl)-2-methylpropanal and 2-Methyl-3(3-(3-methylbut-3-en-1-yl)phenyl)propanal Under argon atmosphere, 3-chloro-2-methylprop-1-ene (10.0 g, 0.110 mol) was added to a stirred suspension of magnesium powder (48.3 g, 200 mol) in anhydrous THF (600 mL). After the reaction had started, further 3-chloro-2-methylprop-1-ene (170 g, 1.88 mol) was added dropwise with stirring and occasional cooling in an ice-bath at such a rate as to keep the temperature between 30-50° C. After complete addition, the reaction mixture was stirred at 60° C. for further 30 min, and then allow to cool down to 25° C. 1-Chloro-3-(chloromethyl)benzene (213 g, 1.32 mol) was added dropwise within 1 h with cooling in an ice-water bath to keep the temperature below 30° C. After complete addition, the reaction was stirred at 70° C. for 1 h, and quenched by pouring the mixture into 1 L of said. q. ammonium chloride in an ice-water bath. The mixture was stirred for 1 h, the organic layer separated and the aqueous one extracted with MTBE (500 mL). The combined organic layers were washed once with brine, and then dried with magnesium sulfate. The solvent was evaporated in a rotatory evaporator, and the crude product dried at 50 mbar/40° C. for 30 min to afford 235 g of a colorless liquid, which was distilled over a 10 cm-glass column with Ar capillary to provide 109 g (45%) of 1-chloro-3-(3-methylbut-3-en-1-yl)benzene as a colorless liquid.

$^1$H NMR (CDCl$_3$): δ=1.75 (s, 3H, CH$_3$), 2.29 (t, J=8.0 Hz, 2H, —CH$_2$—CH$_2$—Ar), 2.72 (t, J=8.0 Hz, 2H, —CH$_2$—AR), 4.69 (s, 1H, =CH$_{2,a}$), 4.74 (s, 1H, =CH$_{2,b}$), 7.03-7.08 (m, 1H, Ar—H), 7.12-7.22 (m, 3H, Ar—H), $^{13}$C NMR (CDCl$_3$): δ=22.6 (q), 33.9 (t), 39.3 (t), 110.6 (t), 126.0 (d), 126.6 (d), 128.5 (d), 129.5 (d), 134.1 (s), 144.2 (s), 144.8 (s). MS: m/z (%)=39 (5), 51 (3), 77 (5), 89 (14), 99 (4), 115 (3), 125 (100), 145 (56), 165 (3), 180 (9) [M$^+$].

Under argon atmosphere, lithium (2.84 g, 410 mmol) was suspended in THF (35 mL) in a 250 mL in rounded-bottomed flask. The colorless suspension was stirred with cooling in an acetone-dry ice bath at −40° C. A solution of 1-chloro-3-(3-methylbut-3-en-1-yl)benzene (36.1 g, 200 mmol) and trimethyl borate (20.8 g, 200 mmol) in THF (25 mL) was added dropwise within 30 min, and the reaction was initiated by allowing occasional warming. After initiation, the reaction temperature was kept below −20° C. for 4 h, prior to removal of the cooling bath and allowing the temperature to raise to room temperature overnight. With most of the lithium metal consumed, the reaction mixture was cooled to 0° C. and carefully quenched by dropwise addition of 5.8% aq. hydrogen chloride (120 mL) with vigorous stirring. Stirring was continued at 5° C.-10° C. for 30 min, before the organic layer was separated. The aqueous layer was extracted twice with MTBE (50 mL each). The combined organic extracts were washed once with brine (50 mL) and then dried with $MgSO_4$. The solvent was removed in a rotatory evaporator, and drying at 50 mbar/40° C. for 30 min, provided 36.6 g (67%) of (3-(3-methylbut-3-en-1-yl) phenyl)boronic acid as a yellowish oil (NMR purity; 70%). The crude material was sufficiently pure to be used in the next steps without further purification.

$^1$H NMR ($CDCl_3$): δ=1.77 (s, 3H, $CH_3$), 2.34 (t, J=7.9 Hz, 2H, —$CH_2$—$CH_2$—AR), 2.79 (t, J=7.9 Hz, 2H, —$CH_2$—Ar), 4.72 (s, 1H, =$CH_{2,a}$), 4.73 (s, 1H, =$CH_{2,b}$), 7.05-7.75 (m, 4H, Ar—H). $^{13}$C NMR ($CDCl_3$): δ=22.7 (q), 34.4 (t), 39.8 (t), 110.4 (t), 127.9 (d), 131.1 (d), 132.4 (d), 134.8 (d), 141.6 (s), 145.3 (s).

[RhCl(cod)]$_2$ (30.0 mg, 0.061 mmol), (1Z,5Z)-cycloocta-1,5-diene (33.0 mg, 0.303 mmol) and potassium phosphate (12.8 g, 60.5 mmol) were added in turn to a stirred solvent mixture of dioxane (180 mL) and water (30 mL) in a 250 mL round-bottomed flask. (3-(3-Methylbut-3-en-1-yl)phenyl) boronic acid (16.4 g, 70% purity, 60.5 mmol) and methacryl aldehyde (6.36 g, 91 mmol) were added to the yellow solution, and the reaction mixture was heated to 90° C. under argon atmosphere for 4 h. The reaction mixture was then allowed to cool to room temperature, diluted with water (75 mL), and extracted with MTBE (2×75 mL). The combined organic layer were washed once with brine, and then dried with $MgSO_4$. The solvent was removed on the rotatory evaporator and the crude product was purified by column chromatography (iso-hexane/MTBE, 20:1) and subsequent Kugelrohr distillation to provide 5.50 g (42%) of 2-methyl-3-(3-(3-methylbut-3-en-1-yl)phenyl)propanal as a colorless odoriferous liquid.

Odor description: floral-aldehydic, watery-marine, sl. metallic.

IR (neat): 2929, 1724, 1450, 886, 786, 703 cm$^{-1}$, $^1$H NMR ($CDCl_3$): δ=1.07 (d, J=6.7 Hz, 3H, CH—$CH_3$), 1.76 (s, 3H, $CH_3$), 2.30 (t, J=8.0 Hz, 2H, —$CH_2$—$CH_2$—Ar), 2.52-2.68 (m, 2H, Ar—$CH_2$—CH($CH_3$)CHO), 2.73 (t, J=8.0 Hz, 2H, —$CH_2$—$CH_2$—Ar), 3.02-3.10 (m, 1H, —CH($CH_3$)—CHO), 4.69 (s, 1, =$CH_{2,a}$), 4.73 (s, 1H, =$CH_{2,b}$), 6.96-7.08 (m, 3H, Ar—H), 7.16-7.25 (m, 1H, Ar—H), 9.69-9.73 (m, 1H, CHO). $^{13}$C NMR ($CDCl_3$): δ=13.2 (q), 22.6 (q), 34.2 (t), 36.7 (t), 39.7 (t), 48.1 (d), 110.3 (t), 126.4 (d), 126.5 (d), 128.5 (d), 129.1 (d), 138.8 (s), 142.5 (s), 145.3 (s), 204.4 (d). MS: m/z (%)=41 (9), 55 (9), 65 (7), 77 (13), 91 (64), 105 (100), 117 (24), 133 (33), 143 (17), 158 (30), 173 (8), 183 (5), 201 (8), 216 (41) [M$^+$].

A solution of 2-methyl-3-(3-(3-methylbut-3-en-1-yl)phenyl)propanal (8.50 g, 39 mmol) in ethyl acetate (100 mL) in a 250 mL round-bottomed flask was degased, and purged with argon. 10%-Palladium on charcoal (800 mg, 0.75 mmol) was added, and the reaction mixture was stirred under hydrogen atmosphere for 2 h until GC-monitoring indicated completion of the conversion. The reaction mixture was filtered through a small pad of silica gel, and the insoluble material was rinsed with ethyl acetate. The filtrates were combined and concentrated on a rotatory evaporator. The resulting residue was distilled in a Kugelrohr apparatus to afford 6.30 g (74%) of 3-3-isopentylphenyl)-2-methylpropanal as a colorless odoriferous liquid.

Odor description: floral-aldehydic, water-marine, sl. fatty-metallic.

IR (neat): 2954, 2869, 1725, 1607, 1487, 1455, 1367, 785, 702 cm$^{-1}$. $^1$H NMR ($CDCl_3$): δ=0.93 (d, J=6.4 Hz, 6H, 2 $CH_3$), 1.07 (d, J=6.8 Hz, 3H, $CH_3$), 1.43-1.65 (m, 3H), 2.52-2.73 (m, 4H), 3.01-3.10 (m, 1H, Ar—CH($CH_3$)—$CH_2$—), 6.94-7.05 (m, 3H, Ar—H), 7.15-7.23 (m, 1H, Ar—H), 9.71 (d, J=1.3 Hz, 1H, CHO). $^{13}$C NMR ($CDCl_3$): δ=13.2 (q), 22.6 (q), 27.8 (d), 33.8 (t), 36.7 (t), 40.9 (t), 48.1 (d), 126.2 (d), 126.5 (d), 128.4 (d), 129.1 (d), 138.8 (s), 143.4 (s), 204.5 (d). MS: m/z (%)=43 (14), 55 (5), 65 (6), 77 (13), 91 (55), 105 (100), 117 (28), 134 (35), 144 (21), 162 (41), 175 (2), 190 (3), 203 (2), 218 (57[M$^+$].

EXAMPLE 3

Alternative route to 2-Methyl-3-(3-(3-methylbut-3-en-1-yl)phenyl)propanal

Under argon atmosphere, in a 750 mL reaction flask, triphenylphosphine (2.00 g, 7.63 mmol), Pd(OAc)$_2$ (500 mg, 2.23 mmol) and copper(I) iodide (400 mg, 2.1 mmol) were dissolved in degassed toluene (300 mL). With vigorous stirring, 3-bromo benzaldehyde (55.5 g, 300 mmol) was added, followed, after 15 min of stirring, by triethylamine (45.0 g, 445 mmol). The reaction mixture was heated to 45° C., upon which an exothermic reaction set in, and the temperature rose to 75° C. within 60 min, with precipitation of (Et)$_3$NHBr. When the exothermic reaction was over, and the temperature started to drop again, the reaction mixture was heated to 90° C. for 10 min., and 2-methylbut-3-yn-2-ol (25.2 g, 300 mmol) was added dropwise over a period of 2 keeping the reaction temperature between 90-95° C. After further 2.75 h of heating to 90-95° C. with stirring, the reaction mixture was allowed to cool to room temperature, and MTBE (300 mL) and water (300 ml) were added cautiously during a period of 10 min. The organic layer was separated, the aqueous one extracted with ether. The combined organic layers were washed with 25% citric acid solution (2×100 mL), washed to pH neutrality, and then dried with $MgSO_4$. The solvent was removed on a rotatory evaporator to afford 76.0 g of crude 3-(3-hydroxy-3-methylbut-1-yn-1-yl)benzaldehyde as a brownish-orange colored liquid. A 15 g sample of this material was purified by Kugelrohr distillation to provide 8.9 g of 3-(3-hydroxy-3-methylbut-1-yn-1-yl)benzaldehyde as an orange-yellowish liquid that was further purified by Kugelrohr distillation to provide 7.2 g (63%) of 3-3-hydroxy-3-methylbut-1-yn-1-yl) benzaldehyde as yellowish liquid.

IR (neat): 2954, 1693, 1598, 1576, 1375, 1362, 1281, 1205, 1164, 1138, 1205, 1164, 1138, 973, 937, 870, 790, 774, 682, 646 cm$^{-1}$. $^1$H NMR ($CDCl_3$): δ=1.65 (s, 6H, 2 $CH_3$), 3.13 (s, 1H, OH), 7.46 (t, J=8.0 Hz, 1H, Ar—H), 7.63 (d, J=8.0 Hz, 1H, Ar—H), 7.78 (d, J=8.0 Hz, 1H, Ar—H), 7.87 (s, 1H, Ar—H), 9.95 (s, 1H, CHO). $^{13}$C NMR ($CDCl_3$): δ=31.3 (2 q), 65.4 (s), 80.5 (s), 95.7 (s), 124.0 (s), 128.9 (d), 129.0 (d), 132.9 (d), 136.2 (s), 137.2 (d), 191.7 (d). MS: m/z (%)=29 (2), 39 (3), 43 (49), 51 (6), 58 (3), 63 (5), 75 (10), 86 (7), 91 (5), 101 (18), 115 (20), 130 (23), 145 (5), 159 (12), 173 (100), 188 (12) [M$^+$]

Palladium on charcoal (10%, 2.00 g, 1.88 mmol) was added to a solution of 3-(3-hydroxy-3-methylbut-1-yn-1-yl) benzaldehyde (15.0 g, 79.7 mmol) and 10 drops of triethylamine in MTBE (45 mL). After 2.5 h of stirring under hydrogen atmosphere at 8 bar/50° C., the catalyst was removed by filtration, and the reaction mixture concentrated in a rotatory evaporator to afford 16.5 g of crude 3-(3-hydroxy-3-methylbutyl)benzaldehyde. Purification by flash chromatography (hexane:MTBE, 2:1) provided 7.20 g (42%) of 3-(3-hydroxy-3-methylbutyl)benzaldehyde. A further flash chromatography (hexane:MTBE, 4:1→3:1) furnished 2.40 g (16%) of pure 3-(3-hydroxy-3-methylbutyl)benzaldehyde.

IR (neat: 2968, 1687, 1585, 1377, 1364, 1238, 1211, 1141, 911, 805, 783, 688, 650 cm$^{-1}$. $^{1}$H NMR (CDCl$_3$): δ=1.31 (s, 6H, (CH$_3$)$_2$C), 1.66 (br. s, 1H, OH), 1.82 (dt, J=7.7, 5.0 Hz, 2H, (CH$_3$)$_2$C(OH)CH$_2$), 2.81 (dt, J=8.7, 5.0 Hz, 2H, CH$_2$Ar), 4.44 (t, J=7.4 Hz, 1H, Ar—H), 7.48 (dt, J=7.4, 1.9 Hz, 1H, Ar—H), 7.70 (dt, J=7.4, 1.9 Hz, 1H, Ar—H), 7.73 (br. s, 1H, Ar—H), 9.99 (s, 1H, CHO). $^{13}$C NMR (CDCl$_3$): δ=29.4 (2 q), 30.4 (t), 45.4 (t), 70.7 (s), 127.6 (d), 129.0 (d), 129.2 (d), 134.6 (d), 136.6 (s), 143.8 (s), 192.6 (d). MS: m/z (%)=27 (2), 31 (5), 39 (7), 43 (15), 51 (8), 59 (100), 65 (16), 77 (20), 91 (88), 105 (56), 115 (7), 119 (84), 131 (52), 145 (30), 159 (17), 174 (85), 177 (23), 192 (6), [M$^+$].

To a solution of 3-(3-hydroxy-3-methylbutyl)benzaldehyde (4.90 g, 25.5 mmol) in methanol (20 mL) was added 2 drops of 15% aq. NaOH solution, which resulted in pH 7.5. Propionaldehyde (2.0 mL, 27.5 mmol) was added, followed by 8 drops of 15% aq. NaOH solution to give pH 9.5 and to initiate and exothermic reaction with the temperature rising to 35° C. After stirring for 20 min. at this temperature another portion of propionaldehyde (2.0 mL, 27.5 mmol) was added, followed by 5 drops of 15% aq. NaOH solution. After stirring for further 35 min., the reaction mixture was neutralized with aq. citric acid, and the product extracted with MTBE. The combined organic layers were washed to pH neutrality, and then dried with MgSO$_4$. The solvent was removed on a rotatory evaporator to afford 7.9 of crude products as a yellow-brownish viscous oil, which was further purified by flash chromatography (hexane:MTBE, 2:1) and distillation to provide at 240° C./100 mbar 3.90 g (66%) of (E)-3-(3-(3-hydroxy-3-methylbutyl)phenyl)-2-methylacrylaldehyde as a yellowish oil.

IR (neat): 2967, 1672, 1622, 1580, 1377, 1360, 1190, 1151, 1017, 913, 700 cm$^{-1}$. $^{1}$H NMR (CDCl$_3$): 1.31 (s, 6H, (CH$_3$)$_2$C), 1.76 (S, 1H, OH), 1.82 (dt, J=7.5, 4.8 Hz, 2H, (CH$_3$)$_2$C(OH)CH$_2$), 2.08 (d, J=1.2 Hz, 3H, C═C—CH$_3$), 2.77 (dt, J=9.1, 4.8 Hz, 2H, CH$_2$Ar), 7.25-7.28 (m, 2H, 2 Ar—H), 7.37 (br. s, 2H, 2 Ar—H), 7.38 (br. s, 1H, Ar—H), 9.57 (s, 1H, CHO). $^{13}$C NMR (CDCl$_3$): δ=11.0 (q), 29.4 (2 q), 30.6 (t), 45.6 (t), 70.7 (s), 127.4 (s), 128.7 (d), 129.7 (d), 130.1 (d), 135.2 (s), 138.2 (s), 143.2 (s), 150.1 (d), 195.6 (d). MS: m/z (%)=43 (8), 59 (32), 65 (5), 77 (6), 91 (20), 115 (29), 129 (24), 145 (48), 158 (100), 171 (8), 181 (5), 199 (15), 214 (21), 232 (2) [M$^+$]

Palladium on charcoal (1.00 g, 0.940 mmol) was added to a solution of (E)-3-(3-(3-hydroxy-3-methylbutyl)phenyl)-2-methylacrylaldehyde (3.0 g, 12.9 mmol) in MTBE (20 mL), and the resulting reaction mixture was stirred for 1 h under hydrogen atmosphere at 1 bar. The catalyst was removed by filtration, and the solvent removed on a rotatory evaporator to afford 3.4 g of crude product, which was purified by distillation to provide at 240° C./80 mbar 2.95 g (98%) of 3-(3-(3-hydroxy-3-methylbutyl)phenyl)-2-methylpropanal as a colorless oil.

IR (neat): 3375, 2968, 2931, 2872, 1717, 1607, 1487, 1455, 1375, 1275, 1208, 1147, 1123, 1092, 1035, 924, 909, 782, 703 cm$^{-1}$. $^{1}$H NMR (CDCl$_3$): δ=1.09 (d, J=7.1 Hz, 3H, CHCH$_3$), 1.28 (s, 6H, (CH$_3$)$_2$C). 1.79 (dt, J=7.6, 4.8 Hz, 2H, (CH$_3$)$_2$C(OH)CH$_2$), 1.98 (br. S, 1H, OH), 2.57 (dd, J=13.4, 8.1 Hz, 1H, CH$_2$CH(CH$_3$)CHO), 2.65-2.72 (m, 3H, Ar—CH$_2$, —CH(CH$_3$)—CHO), 3.06 (dd, J=13.4, 5.8 Hz, 1H, CH$_2$CH(CH$_3$)CHO), 7.00 (d, J=7.3 Hz, 1H, Ar—H), 7.03 (s, 1H, Ar—H), 7.07 (d, J=7.3 Hz, 1H, Ar—H), 7.21 (t, J=7.3 Hz, 1H, Ar—H), 9.69 (d, J=1.2 Hz, 1H, CHO). $^{13}$C NMR (CDCl$_3$): δ=13.2 (q), 29.3 (q), 30.7 (t), 36.6 (t), 45.7 (t), 48.0 (d), 70.8 (s), 126.4 (d), 126.4 (d), 128.5 (d), 129.1 (d), 138.9 (s), 142.9 (s), 204.6 (s). MS: m/z (%)=31 (5), 43 (14), 59 (70), 65 (6), 173 (19), 176 (18), 183 (12), 188 (5), 201 (17, 216 (63) [M$^+$]

para-Toluenesulfonic acid (100 mg, 0.526 mmol) was added to a solution of 3-(3-(3-hydroxy-3-methylbutyl)phenyl)-2-methylpropanal (2.80 g, 11.9 mmol) in toluene (40 mL). The reaction mixture was then refluxed under nitrogen atmosphere for 1.5 h with the water being separated in a Dean-Stark trap, allowed to cool to room temperature, and extracted with hexane. The combined organic extracts were washed with aq. NaHCO$_3$ to pH neutrality and then dried with MgSO$_4$. The solvent was removed on a rotatory evaporator to afford 3.0 g of crude product as a yellowish oil, which was further purified by Kugelrohr distillation to provide at 200° C./0.1 mbar 1.40 g (54% of 2-methyl-3-(3-(3-methylbut-3-en-1-yl)phenyl)propanal as a colorless odoriferous liquid.

Odor description: floral-aldehydic, watery-marine, sl. metallic.

IR (neat): 2929, 1724, 1450, 886, 786, 703 cm$^{-1}$. $^{1}$H NMR (CDCl$_3$): δ=1.07 (d, J=6.7 Hz, 3H, CH—CH$_3$), 7.76 (s, 3H, CH$_3$), 2.30 (t, J=8.0 Hz, 2H, —CH$_2$—CH$_2$—Ar), 2.52-2.68 (m, 2H, Ar—CH$_2$—CH(CH$_3$)CHO), 2.73 (t, J=8.0 Hz, 2H, —CH$_2$—CH$_2$—Ar), 3.02-3.10 (m, 1H, —CH(CH$_3$)—CHO), 4.69 (s, 1H, ═CH$_{2,a}$), 4.73 (s, 1H, ═CH$_{2,b}$), 6.96-7.08 (m, 3H, Ar—H), 7.16-7.25 (m, 1H, Ar—H), 9.69-9.73 (m, 1H, CHO). $^{13}$C NMR (CDCl$_3$): δ=13.2 (q), 22.6 (q), 34.2 (t), 36.7 (t), 39.7 (t), 48.1 (d), 110.3 (t), 126.4 (d), 126.5 (d), 128.5 (d), 129.1 (d), 138.8 (s), 142.5 (s), 145.3 (s), 204.4 (d). MS: m/z (%)=41 (9), 55 (9), 65 (7), 77 (13), 91 (64), 105 (100), 117 (24), 133 (33), 143 (17), 158 (30), 173 (8), 183 (5), 201 (8), 216 (41) [M$^+$].

EXAMPLE 4

3-(3-Isopentylphenyl)butanal

At −30° C., a solution of potassium tert-butoxide (7.73 g, 68.8 mmol) in THF (25 mL) was added to a solution of isobutyl triphenylphosphonium bromide (25.0 g, 62.6 mmol) in THF (100 mL). After 2 h of stirring at this temperature, 3-bromobenzaldehyde was added at −25° C., the cooling bath was removed and the reaction mixture allowed to warm to room temperature. After 3 h of stirring at room temperature, the reaction mixture was poured onto ice-water (1:1). The organic layer was separated, and the aqueous one extracted with ether/The combined organic extracts were washed with water and brine, and then dried with MgSO$_4$. The solvent was removed on a rotatory evaporator to afford 39.9 g of crude product as an orange-brownish liquid, which was further purified by flash chromatography (pentane) to provide 11.1 g (78% of (Z)-1-bromo-3-(3-methylbut-1-enyl)benzene.

IR (neat): 2959, 1592, 1559, 1475, 1069, 886, 788, 746, 712, 699, 680, 664 cm$^{-1}$, $^{1}$H NMR (CDCl$_3$): δ=1.03 (d, J=6.6 Hz, 6H, 2 CH$_3$), 2.80-2.86 (m, 1H, CH(CH$_3$)$_2$), 5.51 (dd, J=11.6, 10.4 Hz, 1H, ═CH—CH(CH$_3$)$_2$), 6.22 (d, J=11.6 Hz, 1H, Ar—CH═C), 7.17-7.20 (m, 2H, 2 Ar—H), 7.33-7.35 (m, 1H, Ar—H), 7.39 (br s, 1H, Ar—H). $^{13}$C NMR (CDCl$_3$): δ=23.0 (2 q), 27.1 (d), 122.2 (s), 125.1 (d), 127.2 (d), 129.4 (d), 129.6 (d), 131.5 (d), 140.0 (s), 141.7 (d). MS: m/z (%)=27 (3), 39 (7), 51 (11), 63 (10), 77 (9), 91 (8), 102 (8), 115 (27), 129 (35), 130 (100), 145 (59), 169 (3), 209 (5), 224 (9) [M$^+$].

A solution of Pd(OAc)$_2$ (88.0 mg, 0.185 mmol), triphenylphosphine (97.0 mg. 0.370 mmol) in DMPU (6.5 mL) was stirred for 10 min., prior to addition of a solution of (Z)-1-bromo-3(3-methylbut-1-enyl)benzene (5.00 g, 22.2 mmol) in DMPU (2.5 mL). After 5 min. of stirring, (E)-but-2-en-1-ol (1.41 g, 18.5 mmol) and sodium hydrogencarbonate (1.90 g, 22.2 mmol) were added. The reaction mixture was heated to 130° C. overnight, and then poured onto ice-water (1:1). After stirring for 5 min. and filtration over Celite, the aqueous phase was extracted with ether. The combined organic extracts were washed with water and brine, and then dried with MgSO$_4$. The solvent was removed on a rotatory evaporator to afford 3.90 g (44%) of (Z)-3-(3-(3-methylbut-1-en-1-yl)phenyl)butanal.

Odor description: floral, marine-watery, aldehydic.

IR (neat): 3001, 1723, 897, 807, 750, 704 cm$^{-1}$, $^1$H NMR (CDCl$_3$): δ=1.05 (d, J=6.6 Hz, 6H, 2 CH$_3$), 1.32 (d, J=7.1 Hz, 3H, Ar—CHR—CH$_3$), 2.65 (ddd, J=16.7, 6.8, 2.0 Hz, 1H, CH$_2$CHO), 2.75 (ddd, J=16.7, 6.8, 2.0H, 1H, CH$_2$CHO), 2.82-2.91 (m, 1H, CH(CH$_3$)$_2$), 3.35 (sext, J=7.1 Hz, 1H, Ar—CHR—CH$_3$), 5.47 (dd, J=11.6, 10.4 Hz, 1H, =CH—CH(CH$_3$)$_2$), 6.28 (d, J=11.6 Hz, 1H, Ar—CH=C), 7.07 (d, J=7.5 Hz, 1H, Ar—H), 7.10 (br s, 1H, Ar—H), 7.12 (d, J=7.5 Hz, 1H, Ar—H), 7.26 (t, J=7.5 Hz, 1H, Ar—H), 9.72 (t, J=2.0 Hz, 1H, CHO), $^{13}$C NMR (CDCl$_3$): δ=22.1 (q), 23.2 (2 q), 27.2 (d), 34.2 (d), 51.7 (t), 124.9 (d), 126.3 (d), 126.8 (d), 127.1 (d), 128.5 (d), 138.2 (s), 140.6 (d), 145.3 (s), 201.8 (d). MS: m/z (%)=29 (4), 41 (11), 69 (7), 77 (9), 91 (25), 105 (13), 115 (33), 129 (5), 145 (22), 157 (100), 172 (20), 183 (7), 201 (3), 216 (27) [M$^+$].

To a solution of (z)-3-(3-(3-methylbut-1-en-1-yl)phenyl) butanal (950 mg, 4.39 mmol) in ethyl acetate (20 mL) was added 10% palladium on charcoal (100 mg, 0.094 mmol). The reaction mixture was stirred under hydrogen atmosphere overnight at ambient pressure. After evacuation of the reaction flask and flushing with argon, the insoluble materials were filtered off, and the solvent was removed on a rotatory evaporator to afford 0.70 g (73%) of 3-(3-isopentylphenyl)butanal, which was purified by flash chromatography (pentane:ether, 19.1; R$_f$ 0.21) to provide 605 mg (60%) of 3-(3-isopentylphenyl)butanal as a colorless, odoriferous liquid.

Odor description: watery-marine, floral, aldehydic, with some ozone-like character.

IR (neat): 2955, 2929, 1724, 1456, 759, 705 cm$^{-1}$, $^1$H NMR (CDCl$_3$): δ=0.94 (d, J=6.8 Hz, 6H, 2 CH$_3$), 1.30 (d, J=7.1 Hz, 3H, Ar—CHR—CH$_3$), 1.46-1.52 (m, 2H, Ar—CH$_2$—CH$_2$R), 1.59 (nonet, J=6.8 Hz, 1H, CH(CH$_3$)$_2$), 2.57-2.61 (m, 2H, Ar—CH$_2$—CH$_2$R), 2.65 (dd, J=16.4, 6.8, 2.0 Hz, 1H, CH$_2$CHO), 2.73 (ddd, J=16.4, 6.8, 2.0 Hz, 1H, CH$_2$CHO), 3.32 (sext, J=7.1 Hz, 1H, Ar—CHR—CH$_3$), 7.01-7.04 (m, 3H, Ar—H), 7.21 (t, J=7.8 Hz, 1H, Ar—H), 9.70 (t, J=2.0 Hz, 1H, CHO). $^{13}$C NMR (CDCl$_3$): δ=22.2 (q), 22.5 (2 q), 27.8 (d), 33.8 (t), 34.3 (d), 40.8 (t), 51.8 (t), 123.9 (d), 126.5 (d), 126.9 (d), 128.6 (d), 143.5 (s), 145.4 (s), 201.8 (d). MS: m/z (%)=29 (6), 43 (17), 55 (4), 65 (5), 71 (7), 77 (10), 91 (56), 105 (53), 118 (100), 129 (17), 134 (11), 147 (69), 162 (12), 175 (14), 176 (23), 203 (9), 218 (49) [M$^+$].

EXAMPLE 5

3-(3-(2-Cyclopropylethyl)phenyl)-2-methylpropanal

At −22° C., a solution of potassium tert-butoxide (1.38 g, 12.3 mmol) in THF (12 mL) was added to a stirred solution of cyclopropyl triphenylphosphonium bromide (4.90 g, 12.3 mmol) in THF (24 mL), upon which the reaction temperature increased to −15° C., and the color cooled to −25° C. and a solution of 3-bromobenzaldehyde (2.28 g, 12.33 mmol) in THF (12 mL) was added, upon which the reaction temperature increased to −4° C. and the color changed to beige. The cooling bath was removed, and the reaction mixture was stirred for 30 min. at room temperature, prior to being poured onto ice-water (1:1). The product was extracted with ether twice, and the combined organic extracts were washed with water, and dried with sodium sulfate. The solvent was removed on a rotatory evaporator to afford 5.79 g of crude product, which was purified by flash chromatography (ether:pentane, 1:100) to provide 1.75 g (61%) of (Z)-1-bromo-3-(2-cyclopropylvinyl)benzene as a yellowish oil.

IR (neat): 1590, 937, 812, 787, 770, 737, 706, 694, 680, 663 cm$^{-1}$. $^1$H NMR (CDCl$_3$): δ=0.46-0.52 (m, 2H, cyclopropyl CH$_{2,a}$). 0.81-0.87 (m, 2H, cyclopropyl CH$_{2,b}$), 1.77-1.87 (m, 1H, cyclopropyl—CH), 5.09 (dd, J=11.5, 10.1H, 1H, Ar—CH=CH—), 6.25 (d, J=11.5 Hz, 1H, Ar—CH=CH—), 7.19 (t, J=7.6 Hz, 1H, Ar—H). $^{13}$C NMR (CDCl$_3$): δ=8.1 (2 1), 11.0 (d), 122.3 (s), 126.0 (d), 127.2 (d), 129.3 (d), 129.7 (d), 131.5 (d), 138.2 (d), 140.1 (s). MS: m/z (%)=27 (2), 39 (4), 51 (4), 57 (2), 63 (7), 70 (3), 75 (5), 89 (6), 102 (5), 115 (29), 128 (100), 143 (55), 193 (2), 207 (2), 222 (10) [M$^+$].

Triphenylphosphine (40.0 mg, 0.152 mmol) was added to a stirred solution of Pd(OAc)$_2$ (36.0 mg, 0.076 mmol) in DMPU (5 mL). After 10 min. of stirring, the color of the clear reaction mixture changed from yellowish to brown. 1-Bromo-3-(2-cyclopropylvinyl)benzene (1.70 g, 7.62 mmol) was added, followed after 3 min. of stirring by sodium hydrogencarbonate (0.768 g, 9.14 mmol) and 2-methylprop-2-en-1-ol (0.659 g, 9.14 mmol). The reaction mixture was refluxed with stirring overnight, allowed to cool to room temperature, poured into ice-water (1:1) and filtered. The filtrate was extracted with ether, and the combined organic extracts were washed with sodium hydrogencarbonate, and dried with magnesium sulfate. The solvent was removed on a rotatory evaporator to afford 1.31 g of crude product, which was purified by flash chromatography (pentane:ether, 98:2) to afford 555 mg (33% of (Z)-3-(3-(2-cyclopropylvinyl)phenyl)-2-methylpropanal as a colorless odoriferous oil.

Odor description: marine, watery floral, green-aldehydic, creamy: slightly reminiscent of egg white.

IR (neat): 1722, 933, 910, 797, 700 cm$^{-1}$. $^1$H NMR (CDCl$_3$): δ=0.45-0.49 (m, 2H, cyclopropyl CH$_{2,a}$), 0.79-0.85 (m, 2H, cyclopropyl CH$_{2,b}$), 1.09 (d, J=6.8 Hz, 3H, —CH(CH$_3$)CHO), 1.81-1.89 (m, 1H, cyclopropyl—CH), 2.60 (dd, J=13.3, 8.3 Hz, 1H, Ar—CH$_{2,a}$—CH(CH$_3$)CHO), 2.67 (qddd, J=8.3, 6.8, 5.5, 1.5 Hz, 1H, Ar—CH$_2$—CH (CH$_3$)CHO), 3.08 (dd, J=13.3, 5.5 Hz, 1H, Ar—CH$_{2,b}$—CH (CH$_3$CHO), 5.05 (d, J=11.6, 9.8 Hz, 1, Ar—CH=CH—), 6.31 (d, J=11.6 Hz, 1H, Ar—CH=CH—), 7.18 (d, J=7.5 Hz, 1H, Ar—H), 7.21 (br. s, 1H, Ar—H), 7.26 (d, J=7.5 Hz, 1H, Ar—H), 7.29 (t, J=7.5 Hz, 1H, Ar—H), 9.72 (d, J=1.5 Hz, 1H, CHO). $^{13}$C NMR (CDCl$_3$): δ=8.0 (2 t), 11.1 (d), 13.2 (q), 36.6 (t), 48.0 (d) 126.2 (d), 127.0 (d), 127.2 (d), 128.3 (d), 129.3 (d), 137.0 (d), 138.2 (s), 138.6 (s), 204.3 (d). MS:

m/z (%)=29 (4), 39 (8), 51 (6), 67 (9), 77 (15), 91 (27), 102 (6), 115 (51), 128 (80), 141 (100), 156 (76), 165 (3), 171 (4), 181 (5), 186 (4), 196 (2), 214 (19), [M$^+$].

Platinum on charcoal (10%, 107 mg, 0.0548 mmol) was added to a solution of 3-(3-(2-cyclopropylvinyl)phenyl)-2-methylpropanal (2.14 g, 10 mmol) in ethanol (40 mL). The reaction flask was evacuated and flushed with argon, evacuated again and flushed with hydrogen. After vigorous stirring overnight at room temperature, the insoluble materials were removed by filtrated over a pad of Celite, which was thoroughly rinsed with ethanol. The solvent was removed on a rotary evaporator to afford 2.25 g of crude product, which was purified by flash chromatography (pentane:ether, 99:1) to provide 550 mg (22%) of 3-(3-(2-cyclopropylethyl)phenyl)-2-methylpropanal as a colorless odoriferous liquid.

Odor description: floral-aldehydic, watery-marine, slightly metallic.

IR (neat): 2922, 1724, 1487, 1014, 780, 702 cm$^{-1}$. $^1$H NMR (CDCl$_3$); δ=0.01-0.03 (m, 2H, cyclopropyl CH$_{2,a}$), 0.37-0.41 (m, 2H, cyclopropyl CH$_{2,b}$), 0.64-0.88 (m, 1H, cyclopropyl CH), 1.05 (d, J=6.8 Hz, 3H, —CH(CH$_3$)CHO), 1.43-1.50 (m, 2H, CH—CH$_2$—CH$_2$), 2.52-2.68 (m, 4H, Ar—CH$_{2,a}$—CH(CH$_3$)CHO, Ar—CH$_2$—CH(CH$_3$) CHO, Ar—CH$_2$CH$_2$—), 3.03 (dd, J=13.6, 6.4 Hz, 1H, Ar—CH$_{2,b}$—CH(CH$_3$)CHO), 6.95 (d, J=7.4 Hz, 1H, Ar—H), 6.97 (s, 1H, Ar—H), 7.02 (d, J=7.4 Hz, 1H, Ar—H), 7.17 (t, J=7.4 Hz, 1H, Ar—H), 9.69 (d, J=1.5 Hz, 1H, CHO). $^{13}$C NMR (CDCl$_3$): δ=4.5 (2 t), 10.7 (d), 13.2 (q), 35.9 (t), 36.7 (t), 36.7 (t), 48.0 (d), 126.3 (d), 126.5 (d), 128.4 (d), 129.2 (d), 138.7 (s), 142.9 (s), 204.4 (d). MS: m/z (%)=29 (11), 41 (19), 55 (60), 65 (11), 77 (22), 91 (85), 105 (100), 117 (72), 129 (64), 143 (33), 158 (51), 159 (51), 173 (7), 183 (5), 188 (9), 198 (4), 215 (7), 216 (4) [M$^+$].

EXAMPLE 6

3-(3-(2-cyclopropylvinyl)phenyl)butanal

A solution of 3-(3-(2-cyclopropylvinyl)phenyl)butanal (2.70 g, 12.6 mmol) in ethyl acetate (50 ml) was stirred in the presence of a catalytic amount of Pd/C (10%) under a hydrogen atmosphere for 15 h. The solution was filtered over a pad of silica gel to yield 3-(3-(2-cycloproplethyl)phenyl)butanal (0.4 g, 13%) as a colorless oil.

Odor description: aldehydic watery floral, marine, slightly buttery, creamy.

IR (neat): 2999, 2924, 2717, 1723, 1605, 1454, 1014, 793, 705 cm$^{-1}$, $^1$H NMR (CDCl$_3$): δ=0.02-0.06 (m, 2H, cyclopropyl CH$_{2,a}$). 0.38-0.44 (m, 2H, cyclopropyl CH$_{2,b}$), 0.65-0.77 (m, 1H, cyclopropyl CH), 1.31 (d, J=6.8 Hz, 3H, —CH(CH$_3$)CH$_2$CHO), 1.47-1.53 (m, 2H, CH—CH$_2$—CH$_2$), 2.56-2.77 (m, 4H, Ar—CH(CH$_3$)CH$_2$CHO, Ar—CH$_2$CH$_2$—), 3.24-3.33 (m, 1H, Ar—CH(CH$_3$) CH$_2$CHO), 7.01-7.05 (m, 3H, Ar—H), 7.19-7.24 (m, 1H, Ar—H), 9.70 (t, J=2.0 Hz, 1, CHO), $^{13}$C NMR (CDCl$_3$): δ=4.5 (2 t), 10.7 (d), 22.2 (q), 34.3 (d), 36.0 (t), 36.7 (t), 51.8 (t), 124.0 (d), 126.7 (d), 127.0 (d), 128.5 (d), 143.1 (s), 145.4 (s), 202.0 (d). MS: m/z (%)=29 (4), 41 (9), 55 (15), 77 (8), 91 (53), 105 (19), 117 (84), 119 (100), 143 (59), 157 (21), 159 (11), 173 (37), 187 (12), 201 (7), 216 (4) [M$^+$].

EXAMPLE 7

2-Methyl-3-(3-(3-methylbut-3-en-1-yl)phenyl)butanal

A mixture of Pd(OAc)$_2$ (158 mg, 0.33 mmol) and triphenyl phosphine (173 mg, 0.66 mmol) in DMPU (20 ml) was stirred at room temperature for 10 min. 1-Bromo-3-(3-methylbut-3-en-1-yl)benzene (7.43 g, 33 mmol) was added to the dark but clear solution. The mixture was stirred for another 3 min and 2-methylbut-2-en-1-ol (5.69 g, 66 mmol) and NaHCO$_3$ (3.33 g, 39.6 mmol) were added. The mixture was heated to 130° C. and left stirring for 15 h at this temperature. The reaction mixture was cooled and poured into ice water (200 ml). The mixture was filtered over a pad of celite and extracted three times with ether. The combined organic phases were washed with water and brine, dried over Na$_2$SO$_4$ and concentrated in vacuo. The residue was purified by chromatography on silica gel and distilled at 145° C./0.13 mbar to yield 2-methyl-3-(3-(3-methylbut-3-en-1-yl)phenyl)butanal (0.75 g, 9%) as a mixture of 2 isomers in a ratio of 6:4 (colorless oil).

Odor description: floral-aldehydic, watery-marine, slightly metallic, dihydro farnesal-like.

IR (neat): 2966, 2931, 2702, 1722, 1751, 885, 780, 705 cm$^{-1}$. $^1$H NMR (CDCl$_3$): δ=0.91, 1.11 (d, J=6.8 Hz, 3H), 1.31, 1.34 (d, J=7.1 Hz, 3H), 1.76 (2s, 3H), 2.32-2.36 (2m, 2H), 2.53-2.68 (2m, 1H), 2.75-2.80 (2m, 2H), 2.97-3.19 (2m, 1H), 4.69 (2bs, 1H), 4.73 (2bs, 1H), 7.01-7.10 (2m, 3H), 7.24-7.28 (2m, 1H), 9.57, 9.68 (d, J=2.1, 3.3 Hz, 1H, CHO). $^{13}$C NMR (CDCl$_3$): δ=10.5, 12.5 (q), 17.5, 20.0 (q), 22.6 (2q), 34.2, 34.3 (t), 39.6 (2t), 40.2, 40.9 (d), 52.5, 52.9 (d), 110.3 (2t), 124.9, 125.0 (d), 126.6 (2d), 127.5, 127.7 (2d), 128.4, 128.5 (d), 142.4, 142.5 (s), 143.6, 144.1 (s), 145.2, 145.3 (s), 204.9 (2d). MS: m/z (%)=29 (6), 41 (11), 55 (7), 65 (4), 77 (9), 91 (47), 105 (15), 117 (99), 119 (100), 145 (23), 157 (10), 159 (11), 173 (56), 187 (8), 197 (4), 215 (2), 230 (6) [M$^+$].

EXAMPLE 8

Feminine Fruity-Floral Fine Fragrance

| Compound/ingredient | parts per weight 1/900 |
|---|---|
| 1. ALLYL AMYL GLYCOLATE | 1.00 |
| 2. AMBROFIX (dodecahydro-3a,6,6,9a-tetramethyl-naphthol[2,1-b]furan) | 2.00 |
| 3. BENZYL SALICYLATE | 100.00 |
| 4. CITRONELLYL ACETATE | 10.00 |
| 5. 1,1-DIMETHYL-2-PHENYLETHYL BUTYRATE | 3.00 |
| 6. DIPROPYLENE GLYCOL (DPG) | 85.00 |
| 7. ETHYLENE BRASSYLATE | 90.00 |
| 8. FLOROSA (TETRAHYDRO-4-METHYL-2-(2-METHYLPROPYL)-2H-PYRAN-4-OL) | 85.00 |
| 9. GARDENOL (METHYL PHENYL CARBINYL ACETATE) | 5.00 |
| 10. GEORGYWOOD (2-acetyl-1,2,3,4,5,6,7,8-octahydro-1,2,8,8-tetramethylnaphthalene) | 200.00 |
| 11. GRAPEFRUIT OIL COSMOS | 70.00 |

| Compound/ingredient | parts per weight 1/900 |
|---|---|
| 12. CIS-3-HEXENOL | 3.00 |
| 13. CIS-3-HEXENYL SALICYLATE | 25.00 |
| 14. LEMON OIL ITALY ORPUR | 45.00 |
| 15. LIFFAROME (3Z-HEXENYL METHYL CARBONATE), 10% DPG | 8.00 |
| 16. LINALYL ACETATE | 45.00 |
| 17. ORANGE OIL BRASIL | 25.00 |
| 18. PEPPERWOOD (3,7-dimethylocta-1,6-dien-3-yl dimethylcarbamate) | 20.00 |
| 19. PETALIA (2-cyclohexylidene-2-(o-tolyl)-acetonitrile) | 25.00 |
| 20. POMAROSE ((2E)-5,6,7-trimethylocta-2,5-dien-4-one), 10% DPG | 3.00 |
| 21. SERENOLIDE (2-(1-(3,3-dimethylcyclohexyl)-ethoxy)-2-methylpropyl cyclopropane-carboxylate) | 35.00 |
| 22. 3-(3-(4-Methylpentyl)phenyl)butanal | 15.00 |
| Total: | 900.00 |

The introduction of 1.67% of 3(3-(4-methylpentyl)phenyl)butanal provides this feminine-fruity-floral fine fragrance composition with a watery, aquatic-floral effect and a unique marine, even slightly salty signature. In effect, the volume, thickness and olfactory density of the perfume are significantly increased, and the creaminess as well as floralcy is enhanced. Using the more potent (S)-configured isomer of 3-(3-(4-methylpentyl)phenyl)butanala (87% ee, Example 1) instead of the racemic material at the same quantity increases the floral-watery effect even further to a point where the composition turns completely into a buttery creaminess. This effect can however even be perceived as too dominant, and the weaker (R)-configured isomer of 3-(3-(4-methylpentyl)phenyl)butanal (84% ee) with its watery, aquatic-floral note more in a sweet fruity, melon direction, might esthetically be preferred. Employing 15% of (R)-3-(3-(4-methylpentyl)phenyl)butanal (84% ee) instead of the racemic material also induces an aquatic floralcy, but keeps the transparency high, and adds rather a sweet fruity-marine melon-type twist to the composition. All three materials, the racemate of 3-(3-(4-methylpentyl)phenyl)butanal as well as its individual stereoisomers provide a distinct and characteristic marine, aquatic-flora signature to this modern, floral feminine fine fragrance.

EXAMPLE 9

Floral-Fruity Unisex Fragrance for Use as Perfume and in Cosmetics

| Compound/Ingredient | Parts per Weight 1/900 |
|---|---|
| 1. CALONE 1951 (7-methyl-2H-benzo[b][1,4]-dioxepin-3(4H)-one) | 3.00 |
| 2. CASSYRANE (2-(tert-butyl)-5-methyl-2-propyl-2,5-dihydrofuran), 10% DPG | 25.00 |
| 3. CEPIONATE (methyl 2-(3-oxo-2-pentylcyclopentyl)-acetate) | 280.00 |
| 4. CITRONELLYL ACETATE | 10.00 |
| 5. CYCLAL C (2,4-dimethylcyclohex-3-ene-carbaldehyde) | 4.00 |
| 8. DIHYDRO MYRCENOL | 25.00 |
| 7. DIPROPYLENE GLYCOL (DPG) | 77.00 |
| 8. ETHYLENE BRASSYLATE | 45.00 |
| 9. FLOROSA (2-isobutyl-4-methyltetrahydro-2H-pyran-4-ol) | 70.00 |
| 10. FLORYMOSS (1-(cyclooct-3-en-1-yl)propan-1-ol) | 80.00 |
| 11. GALBANONE 10 (1-(3,3/5,5-dimethylcyclo-hex-1-en-1-yl)pent-4-en-1-one) | 8.00 |
| 12. GARDENOL (METHYL PHENYL CARBINYL ACETATE) | 15.00 |
| 13. CIS-3-HEXENOL | 1.00 |
| 14. LINALOOL SYNTHETIC | 45.00 |
| 15. MAGNOLIA FLOWER OIL CHINA ORPUR | 1.00 |
| 16. MANDARINE OIL ITALY COLORLESS, MOL DIST | 45.00 |
| 17. MAYOL ((4-isopropylcyclohexyl)methanol) | 90.00 |
| 18. OKOUMAL (2,4-dimethyl-2-(5,5,8,8-tetramethyl-5,6,7,8-tetrahydronaphthalen-2-yl)-1,3-dioxolane) | 4.00 |
| 19. PETALIA (2-cyclohexylidene-2-(o-tolyl)-acetonitrile) | 10.00 |
| 20. ROSE OXIDE (2-isobutenyl-4-methyl-tetrahydropyran) | 1.00 |
| 21. TROPIONAL (3-(benzo[d][1,3]dioxol-5-yl)-2-methylpropanal) | 35.00 |
| 22. VIOLET NITRILE (2,6-nonadienenitrile) 10% TEC, 1% DPG | 1.00 |
| 23. 3-(3-Isopentylphenyl)-2-methyl-propanal | 25.00 |
| Total: | 900.00 |

The introduction of 2.78% of 3-(3-isopentylphenyl)-2-methylpropanal much enhances the fruitiness and the floral lily-of-the-valley character of the composition. Thus, it provides a mouthwatering, transparent fruity-floral aquatic feeling as well as body, creaminess and volume to the composition. With the floral-marine aquatic note of 3-(3-isopentylphenyl)-2-methylpropanal the fragrance formulation becomes less opaque, but instead appears fresh, light and watery. This highlights especially juicy fruity aspects, but also watery floralcy of this perfume composition.

EXAMPLE 10

Fresh Marine-Woody Masculine Fine Fragrance

| Compound/Ingredient | Parts per Weight 1/900 |
|---|---|
| 1. BERGAMOT OIL ITALY ORPUR | 25.00 |
| 2. CALYPSONE (6-Methoxy-2,6-dimethyloctanal) | 20.00 |
| 3. CEPIONATE (methyl 2-(3-oxo-2-pentylcyclopentyl)-acetate) | 150.00 |
| 4. CITRONELLOL EXTRA | 25.00 |
| 5. DIPROPYLENE GLYGOL (DPG) | 138.00 |
| 6. ETHYLENE BRASSYLATE | 90.00 |
| 7. ETHYL SAFRANATE (ethyl 2,6,6-trimethylcyclo-hexa-1,3-diene-1-carboxylate), 10% DPG | 8.00 |
| 8. FLORYMOSS (1-(cyclooct-3-en-1-yl)propan-1-ol) | 45.00 |
| 9. GEORGYWOOD (2-acetyl-1,2,3,4,5,6,7,8-octahydro-1,2,8,8-tetramethylnaphthalene) | 20.00 |
| 10. HERBOXANE (2-Butyl-4,4,6-trimethyl-1,3-dioxane) | 75.00 |
| 11. CIS-3-HEXENYL SALICYLATE | 25.00 |
| 12. ISORALDEINE CETONE ALPHA (3-Methyl-4-(2,6,6-tri-Methyl-2-cyclohexen-1-yl)-3-buten-2-one) | 45.00 |
| 13. LEMON OIL ITALY ORPUR | 55.00 |
| 14. MANZANATE (Ethyl 2-methylpentanoate), 1% DPG | 25.00 |
| 15. GAMMA-OCTALACTONE, 10% DPG | 3.00 |
| 16. OSYROL (7-methoxy-3,7-dimethyloctan-2-ol) | 20.00 |
| 17. ROSALVA (dec-9-en-1-ol), 10% DPG | 8.00 |
| 18. ROSSITOL (1-methyl-3-(2-methylpropyl)-cyclohexanol) | 35.00 |
| 19. SERENOLIDE (2-(1-(3,3-dimethylcyclohexyl)-ethoxy)-2-methylpropyl cyclopropane-carboxylate) | 80.00 |
| 20. 2-methyl-3-(3-(3-methylbut-3-en-1-yl)phenyl)-propanal | 8.00 |
| Total: | 900.00 |

The introduction of only 0.89% of 2-methyl-3-(3-(3-methylbut-3-en-1-yl)phenyl)propanal already induces a pleasant transparency and floralcy to this marine masculine perfume composition, and much enhances its freshness and aquatic marine character. One can even notice a salty character that is introduced, and very well accompanies the overall marine-watery feeling. Also the seed-like quality of the perfume composition is highlighted by the use of this minor amount of 2-methyl-3-(3-(3-methylbut-3-en-1-yl)phenyl)propanal.

EXAMPLE 11

Green Lily-of-the-Valley Theme for Use as Perfume and in Cosmetics

| Compound/Ingredient | Parts per Weight 1/900 |
|---|---|
| 1. BENZYL ACETATE EXTRA | 40.00 |
| 2. CITRONELLYL ACETATE | 75.00 |
| 3. CITRONELLOL | 25.00 |
| 4. COSMONE (3-methyl-cyclotetradec-5-en-1-one) | 10.00 |
| 5. DIPROPYLENE GLYCOL (DPG) | 130.00 |
| 6. ETHYL LINALOOL | 25.00 |
| 7. EVERNYL (methyl 2,4-dihydroxy-3,6-dimethylbenzoate) | 1.00 |
| 8. FLOROSA (tetrahydro-4-methyl-2-(2-methylpropyl)-2h-pyran-4-ol) | 55.00 |
| 9. FLORYMOSS (1-(cyclooct-3-en-1-yl)propan-1-ol) | 25.00 |
| 10. HEDIONE HIGH CIS (CIS-methyl 2-(3-oxo-2-pentyl-cyclopentyl)acetate) | 55.00 |
| 11. 3-CIS-HEXENOL | 7.00 |
| 12. HYDROXYCITRONELLAL | 45.00 |
| 13. INDOL PURE, 10% DPG | 8.00 |
| 14. JASMIN ABSOLUT EGYPT PURE | 12.00 |

-continued

| Compound/Ingredient | Parts per Weight 1/900 |
|---|---|
| 15. CIS-JASMONE | 15.00 |
| 16. JASMOPYRANE FORTE ((3-pentyloxan-4-yl)acetate) | 25.00 |
| 17. LEMON OIL ITALY ORPUR | 10.00 |
| 18. PEPPERWOOD (3,7-dimethylocta-1,6-dien-3-yl dimethylcarbamate) | 10.00 |
| 19. PETALIA (2-cyclohexylidene-2-(o-tolyl)-acetonitrile) | 45.00 |
| 20. 2-PHENYLETHANOL | 200.00 |
| 21. ROSE OIL BULGARIA ORPUR | 2.00 |
| 22. VIOLET NITRILE (2,6-nonadienenitrile) 10% TEC, 1% DPG | 10.00 |
| 23. VIRIDINE (2,2-dimethoxyethylbenzene) | 25.00 |
| 24. YLANG YLANG OIL MADAGASCAR | 20.00 |
| 25. 3-(3-Isopentylphenyl)butanal | 25.00 |
| Total: | 900.00 |

The addition of 2.78% of 3-(3-isopentylphenyl)butanal provides this lily-of-the-valley fragrance formulation with a natural green, aquatic-floral freshness, highlighting the central floral theme. It also significantly enhances its volume and lends the perfume more body, thus making it appear more full, yet still transparent and light.

The invention claimed is:

1. A compound of the formula (I)

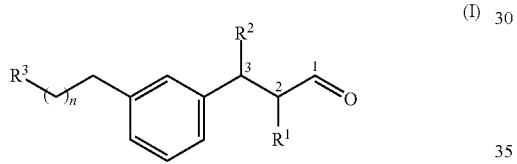

wherein
R$^1$ and R$^2$ are independently selected from hydrogen and methyl with the proviso that at least either R$^1$ or R$^2$ is methyl;
R$^3$ is selected from prop-2-yl, propen-2-yl and cyclopropyl; and
n is 1 or 2.

2. The compound according to claim 1 selected from 3-(3-(4-methylpentyl)phenyl)butanal, 3-(3-isopentylphenyl)-2-methylpropanal, 2-methyl-3-(3-(3-methylbut-3-en-1-yl)phenyl)-propanal, 3-(3-isopentylphenyl)butanal, 3-(3-(2-cyclopropyl ethyl)phenyl)-2-methylpropanal, 3-(3-(2-cyclopropylethyl)phenyl)butanal, and 2-methyl-3-(3-(3-methylbut-3-en-1-yl)phenyl)butanal.

3. The compound according to claim 1 wherein R$^2$ is methyl.

4. The compound according to claim 1 enriched in the (5) enantiomer.

5. A method comprising utilizing as a fragrance the compound of formula (I)

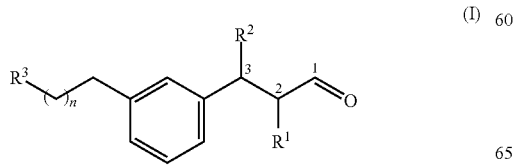

wherein
R$^1$ and R$^2$ are independently selected from hydrogen and methyl with the proviso that at least either R$^1$ or R$^2$ is methyl;
R$^3$ is selected from prop-2-yl, propen-2-yl and cyclopropyl; and
n is 1 or 2.

6. A method for improving, enhancing or modifying a consumer product base by means of the addition thereto a compound of formula (I), or a mixture thereof

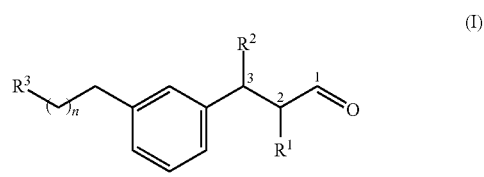

wherein
R$^1$ and R$^2$ are independently selected from hydrogen and methyl with the proviso that at least either R$^1$ or R$^2$ is methyl;
R$^3$ is selected from prop-2-yl, propen-2-yl and cyclopropyl; and
n is 1 or 2.

7. A fragrance composition comprising
a. at least one compound of formula (I)

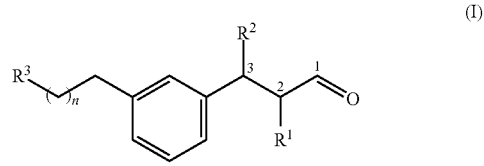

wherein
R$^1$ and R$^2$ are independently selected from hydrogen and methyl with the proviso that at least either R$^1$ or R$^2$ is methyl;
R$^3$ is selected from prop-2-yl, propen-2-yl and cyclopropyl; and
n is 1 or 2;
b. and at least one other odorant.

8. A fragranced article comprising
a. at least one compound of formula (I)

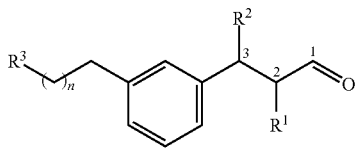

wherein
$R^1$ and $R^2$ are independently selected from hydrogen and methyl with the proviso that at least either $R^1$ or $R^2$ is methyl;
$R^3$ is selected from prop-2-yl, propen-2-yl and cyclopropyl; and
n is 1 or 2;
b. and a consumer product base.

9. The method according to claim 5 wherein the compound of formula (I) is selected from 3-(3-(4-methylpentyl)phenyl)butanal, 3-(3-isopentylphenyl)-2-methylpropanal, 2-methyl-3-(3-(3-methylbut-3-en-1-yl)phenyl)-propanal, 3-(3-isopentylphenyl)butanal, 3-(3-(2-cyclopropyl ethyl)phenyl)-2-methylpropanal, 3-(3-(2-cyclopropylethyl)phenyl)butanal, and 2-methyl-3-(3-(3-methylbut-3-en-1-yl)phenyl)butanal.

10. The method according to claim 6 wherein the compound of formula (I) is selected from 3-(3-(4-methylpentyl)phenyl)butanal, 3-(3-isopentylphenyl)-2-methylpropanal, 2-methyl-3-(3-(3-methylbut-3-en-1-yl)phenyl)-propanal, 3-(3-isopentylphenyl)butanal, 3-(3-(2-cyclopropylethyl)phenyl)-2-methylpropanal, 3-(3-(2-cyclopropylethyl)phenyl)butanal, and 2-methyl-3-(3-(3-methylbut-3-en-1-yl)phenyl)butanal.

11. The fragrance composition according to claim 7 wherein the compound of formula (I) is selected from 3-(3-(4-methylpentyl)phenyl)butanal, 3-(3-isopentylphenyl)-2-methyl propanal, 2-methyl-3-(3-(3-methylbut-3-en-1-yl)phenyl)-propanal, 3-(3-isopentyl phenyl)butanal, 3-(3-(2-cyclopropylethyl)phenyl)-2-methylpropanal, 3-(3-(2-cyclopropylethyl)phenyl)butanal, and 2-methyl-3-(3-(3-methylbut-3-en-1-yl)phenyl)butanal.

12. The fragranced article according to claim 8 wherein the compound of formula (I) is selected from 3-(3-(4-methylpentyl)phenyl)butanal, 3-(3-isopentylphenyl)-2-methylpropanal, 2-methyl-3-(3-(3-methylbut-3-en-1-yl)phenyl)-propanal, 3-(3-isopentylphenyl) butanal, 3-(3-(2-cyclopropylethyl)phenyl)-2-methylpropanal, 3-(3-(2-cyclopropyl ethyl)phenyl)butanal, and 2-methyl-3-(3-(3-methylbut-3-en-1-yl)phenyl)butanal.

* * * * *